United States Patent
Tao et al.

(10) Patent No.: US 8,383,879 B2
(45) Date of Patent: Feb. 26, 2013

(54) NON-HUMAN ANIMAL DISEASE MODE FOR HEPATITIS B VIRUS-ASSOCIATED DISEASE

(75) Inventors: Mi-Hua Tao, Taipei (TW); Cheng-Chieh Fang, Pingtung County (TW); Ya-Hui Huang, Taipei County (TW)

(73) Assignee: Academia Sinica, Taipei (TW)

( * ) Notice: Subject to any disclaimer, the term of this patent is extended or adjusted under 35 U.S.C. 154(b) by 111 days.

(21) Appl. No.: 12/959,632

(22) Filed: Dec. 3, 2010

(65) Prior Publication Data
US 2011/0136100 A1    Jun. 9, 2011

Related U.S. Application Data

(60) Provisional application No. 61/266,519, filed on Dec. 4, 2009.

(51) Int. Cl.
*A01K 67/00* (2006.01)
*C12N 15/864* (2006.01)

(52) U.S. Cl. ............ 800/13; 424/93.1; 135/320.1

(58) Field of Classification Search .......... None
See application file for complete search history.

(56) References Cited

PUBLICATIONS

Crettaz et al. J. Virol. published on Dec. 30, 2008.*
Tennant et al. Gastreonterology 2004, vol. 127, issue 5, supplemental 1, pp. S283-S293.*
Liu et al. World J. Gastroenterology, Oct. 2007, vol. 13)4), pp. 5324-5330.*
La Sorsa et al. Virus Gene, 2002, vol. 25, No. 2, pp. 147-157.*
Zazkman in NCBI Bookshelf. A service of the National Library of Medicine, National Institutes of Health. Baron S, editor. Medical Microbiology. 4th edition. Galveston (TX): University of Texas Medical Branch at Galveston; 1996, pp. 1-19.*
Lai et al., (2006) "Synthetic intron improves transduction efficiency of trans-splicing adeno-associated viral vectors" Hum Gene Ther 17, 1036-1042.
Lai et al., (2005) "Efficient in vivo gene expression by trans-splicing adeno-associated viral vectors". Nat Biotechnol 23, 1435-1439.
Nakamoto et al. (1998) "Immune pathogenesis of hepatocellular carcinoma" J Exp Med 188 341-350.
Newell et al. (2008) "Experimental models of hepatocellular carcinoma" J Hepatol 48, 858-879.
Keng et al. (2009) "A conditional transposon-based insertional mutagenesis screen for genes associated with mouse hepatocellular carcinoma" Nat Biotechnol 27, 264-274.

* cited by examiner

*Primary Examiner* — Bao Li
(74) *Attorney, Agent, or Firm* — Hsiu-Ming Saunders; Intellectual Property Connections, Inc.

(57) ABSTRACT

A non-human animal disease model for hepatitis B virus-associated liver disease is disclosed. The animal disease model is transduced with a hepatitis B virus genome in the liver cells thereof and exhibits the following symptoms: hepatitis B viral particles and hepatitis B viral DNA in the serum, hepatitis B virus (HBV) envelope and HBV e proteins in the serum, expression of HBV core and HBV envelope proteins in the liver but not in the kidney, heart, lung, brain, pancreas, spleen, stomach or intestine tissues. The animal disease model may develop hepatocellular carcinoma, exhibiting an elevated level of alanine aminotransferase as compared to a control animal without the hepatitis B virus genome in the liver cells thereof, and liver pathological symptoms such as tumor nodules, dysplasia, inflammatory infiltrates, necrosis and fibrosis.

19 Claims, 14 Drawing Sheets

SEQUENCE LISTING

```
<160> NUMBER OF SEQ ID NOS: 8

<210> SEQ ID NO 1
<211> LENGTH: 28
<212> TYPE: DNA
<213> ORGANISM: Artificial Sequence
<220> FEATURE:
<223> OTHER INFORMATION: 5'-HBV donor fragment forward primer

<400> SEQUENCE: 1
aaaaagctta tgtattcaat ctaagcag                                      28
```

-continued

<210> SEQ ID NO 2
<211> LENGTH: 69
<212> TYPE: DNA
<213> ORGANISM: Artificial Sequence
<220> FEATURE:
<223> OTHER INFORMATION: 5'-HBV donor fragment reverse primer

<400> SEQUENCE: 2
tttctcgagt attggtctcc ttaaacctgt cttgtaacct tgatacttac ctgaactgga    60
gccaccagc                                                            69

<210> SEQ ID NO 3
<211> LENGTH: 93
<212> TYPE: DNA
<213> ORGANISM: Artificial Sequence
<220> FEATURE:
<223> OTHER INFORMATION: 3'-HBV acceptor fragment forward primer

<400> SEQUENCE: 3
aaagaattcc tcttgcgttt ctgataggca cctattggtc ttactgacat ccactttgcc    60
tttctctcca caggaacagt aaaccctgtt ctg                                 93

<210> SEQ ID NO 4
<211> LENGTH: 29
<212> TYPE: DNA
<213> ORGANISM: Artificial Sequence
<220> FEATURE:
<223> OTHER INFORMATION: 3'-HBV acceptor fragment reverse primer

<400> SEQUENCE: 4
tttgtcgact actgaaggaa agaagtcag                                      29

<210> SEQ ID NO 5
<211> LENGTH: 18
<212> TYPE: DNA
<213> ORGANISM: Artificial Sequence
<220> FEATURE:
<223> OTHER INFORMATION: PCR forward primer for HBV DNA

<400> SEQUENCE: 5
ctccaccaat cgccagtc                                                  18

<210> SEQ ID NO 6
<211> LENGTH: 24
<212> TYPE: DNA
<213> ORGANISM: Artificial Sequence
<220> FEATURE:
<223> OTHER INFORMATION: PCR reverse primer for HBV DNA

<400> SEQUENCE: 6
atcctcgaga agattgacga taat                                           24

<210> SEQ ID NO 7
<211> LENGTH: 26
<212> TYPE: DNA
<213> ORGANISM: Artificial Sequence
<220> FEATURE:
<223> OTHER INFORMATION: 3' fluorescein labeled donor probe

<400> SEQUENCE: 7
catggcctga ggatgagtgt ttctca                                         26

<210> SEQ ID NO 8
<211> LENGTH: 21

-continued

```
<212> TYPE: DNA
<213> ORGANISM: Artificial Sequence
<220> FEATURE:
<223> OTHER INFORMATION: 5' Red640 labeled acceptor probe

<400> SEQUENCE: 8
aggtggagac agcggggtag g                                              21
```

US 8,383,879 B2

NON-HUMAN ANIMAL DISEASE MODE FOR HEPATITIS B VIRUS-ASSOCIATED DISEASE

REFERENCES TO RELATED APPLICATION

The present application claims priority to U.S. Provisional Application Ser. No. 61/266,519, filed Dec. 4, 2009, which is herein incorporated by reference in its entirety.

FIELD OF THE INVENTION

The present invention relates generally to an animal disease model, and more specifically to a non-human animal model for hepatitis B virus-associated disease, and methods of making and using the same.

BACKGROUND OF THE INVENTION

HBV chronically infects 400 million people worldwide and leads to a high incidence of severe liver complications, including cirrhosis and hepatocellular carcinoma (HCC), in these patients. HCC is a leading cause of death worldwide and is one of the most difficult cancers to treat, only a small number of patients qualifying for curative therapies.

It is believed that HBV itself is not highly cytopathic and that the chronic liver injury and HCC development are secondary to an antiviral cellular immune response. However, progress in understanding the immunopathogenic mechanisms of HBV-associated liver diseases has been hampered by the lack of a convenient small animal model. Chimpanzees are susceptible to HBV infection, but only develop a mild liver inflammatory reaction, and their use in laboratory research is further limited because of ethical and financial considerations. Studies of HBV-related viruses in woodchucks, ground squirrels, and ducks have improved our knowledge of HBV virology and the development of antiviral agents, but have not led to a better understanding of HBV immunopathology. Similarly, HBV transgenic mice produce infectious HBV from the chromosome-integrated viral genome, but are centrally tolerant to viral antigens and do not develop liver diseases. A refinement of this latter system, involving the injection of immunocompetent mice with a plasmid containing a full-length HBV genome, resulted in transient or long-term HBV replication in the liver, but caused only limited hepatitis. Adoptive transfer of unprimed splenocytes into HBV transgenic mice on a severe combined immunodeficiency background generated chronic hepatitis with fluctuations in alanine aminotransferase (ALT) levels but the liver disease was mild and did not progress to HCC, possibly due to the lack of regeneration of HBV-specific T cells in the host.

Therefore, there is an urgent need to produce a chronic HBV disease model in an immune competent animal to facilitate elucidating the cause-and-effect relationships of chronic HBV diseases.

SUMMARY OF THE INVENTION

In one aspect, the invention relates to a non-human animal disease model for hepatitis B virus-associated liver disease, in which the animal disease model comprises a hepatitis B virus genome in the liver cells thereof and exhibits the following symptoms: a) hepatitis B viral particles in the serum; b) hepatitis B viral DNA in the serum; c) hepatitis B virus (HBV) envelope and HBV e proteins in the serum; and d) expression of hepatitis B virus (HBV) core and HBV envelope proteins in the liver but not in the kidney, heart, lung, brain, pancreas, spleen, stomach or intestine tissues thereof.

In one embodiment of the invention, the hepatitis B virus genome is transduced into the liver cells with an adenovirus-associated vector (AAV) comprising a hepatitis B virus genomic DNA insert.

In another embodiment of the invention, the hepatitis B virus genome is transduced into the liver cells with two adeno-associated virus (AAV) vectors, each carrying a different fragment of the HBV genome, which together produce a functional HBV genome in the liver cells thereof.

In another embodiment of the invention, the aforementioned non-human animal disease model for hepatitis B virus (HBV)-associated liver disease further exhibits at least one of the following serological and immunological responses in the serum: a) HBV envelope antigen; b) hepatitis B e antigen; and c) an increase in hepatitis B envelope-specific CD8+ T cells in the liver and/or spleen as compared to a control animal without the hepatitis B virus genome in the liver cells thereof.

In another embodiment of the invention, the aforementioned non-human animal disease model for hepatitis B virus (HBV)-associated liver disease further exhibits a chronic hepatitis B serological profile as follows: a) negative for anti-hepatitis B envelope antibody; b) negative for anti-hepatitis B e antibody; and c) positive for anti-hepatitis B core antibody.

Further in another embodiment of the invention, the aforementioned non-human animal disease model for hepatitis B virus (HBV)-associated liver disease further exhibits at least one of the following immunopathological responses: a) inflammatory infiltration in the liver tissues; b) mitosis in the liver tissues; c) acidophilic nuclear inclusions in the hepatocytes; d) expression of hepatitis B core protein in the hepatocytes; e) expression of hepatitis B envelope protein in the hepatocytes; and f) an increase in the level of alanine aminotransferase as compared to that of a control animal without the hepatitis B virus genome in the liver cells thereof.

In another embodiment of the invention, the hepatitis B virus-associated liver disease is hepatocellular carcinoma and the animal disease model exhibits at least one of following liver pathological changes: a) liver tumor nodules; b) positive for fibrinogen in the liver tissues; c) liver dysplasia; d) inflammatory infiltrates in the liver; e) necrosis of hepatocytes; f) liver fibrosis; and g) an increase in the level of alanine aminotransferase as compared to that of a control animal without the hepatitis B virus genome.

In another embodiment of the invention, the aforementioned non-human animal disease model for hepatitis B virus (HBV)-associated liver disease is a rodent. The rodent may be a mouse chosen from BALB/c, ICR, C57BL/6 and FVB strains.

In another embodiment of the invention, the aforementioned non-human animal disease model for hepatitis B virus (HBV)-associated liver disease is immune competent.

In another embodiment of the invention, the germ line of the aforementioned non-human animal disease model for hepatitis B virus (HBV)-associated liver disease does not comprise a hepatitis B virus genome.

In another aspect, the invention relates to a non-human animal disease model for hepatocellular carcinoma, comprising a hepatitis B virus genome in the liver cells thereof and exhibiting at least one of the following symptoms: a) liver tumor nodules; b) liver dysplasia; c) inflammatory infiltrates in the liver; d) steatosis and necrosis of hepatocytes; e) liver fibrosis; and f) an increase in the level of alanine aminotransferase as compared to that of a control animal without the hepatitis B virus genome.

Further in another aspect, the invention relates to a method of generating a non-human animal disease model for hepatitis B virus-associated liver disease as aforementioned. The method comprises: a) obtaining a non-human animal; and b) administering to the animal a composition comprising: a first adeno-associated viral vector comprising 5' genomic DNA fragment of a hepatitis B virus, and a second adeno-associated viral vector comprising 3' genomic DNA fragment of the hepatitis B virus; and c) allowing the animal develops symptoms associated with the hepatitis B virus-associated liver disease.

In one embodiment of the invention, the aforementioned administering step is replaced by: administering to the animal a composition comprising an adeno-associated viral vector comprising a hepatitis B virus genomic DNA.

In another embodiment of the invention, the non-human animal in the aforementioned method is an immune competent mouse.

Further in another aspect, the invention relates to a method for screening for a therapeutic agent effective in treating hepatitis B virus-associated liver disease, comprising: a) providing a non-human animal disease model for hepatitis B virus-associated liver disease as aforementioned; b) administering to the animal disease model an agent to be tested for therapeutic effectiveness; and c) determining whether the agent is effective for treating the hepatitis B virus-associated liver disease.

In one embodiment of the invention, the invention relates to a method for screening for a therapeutic agent effective in treating hepatocellular carcinoma, comprising: a) providing a non-human animal disease model for hepatocellular carcinoma as aforementioned; b) administering to the animal disease model a compound to be tested for therapeutic effectiveness; and d) determining whether the compound is effective for treating the hepatocellular carcinoma.

BRIEF DESCRIPTION OF THE DRAWINGS

FIG. 1A is a schematic diagram of the trans-splicing AAV vectors. AAV/5'-HBV-SD contains the 5'-half of the 1.3× HBV genome and the splice donor (SD) sequence, while AAV/3'-HBV-SA contains the splice acceptor (SA) sequence followed by the 3'-half of the 1.3× HBV genome. The 1.3× HBV genome and HBV open reading frames are also shown. The split site on the HBV genome is indicated by an arrow. En, enhancer; pA, polyadenylation signal. FIG. 1B shows comparisons of natural HBV infection and AAV/HBV transduction. In natural HBV infection of human hepatocytes (left panel), HBV virions bind to surface receptors (identity currently unknown), leading to uncoating and transport of the capsid to the nucleus. The partially double-stranded HBV genome is repaired and converted to a covalently closed circular DNA (cccDNA) molecule, which serves as the transcriptional template to product the 3.5 kb pregenomic RNA and other viral mRNAs. The viral mRNAs are translated in the cytoplasm to produce core, surface, polymerase, and X proteins, followed by assembly and production of new HBV virions, which are then released to initiate new infection. For AAV/HBV transduction of mouse hepatocytes (right panel), the two AAV vectors, carrying either the 5'-half or 3'-half of the HBV genome, enter cells through receptor (laminin receptor)-mediated endocytosis and trafficking to the nucleus, probably through a process involving endosomes. Once in the nucleus, the full length HBV genome can be reconstituted in the concatamer DNA by AAV inverted terminal repeat-mediated head-to-tail intermolecular recombination. Functional HBV pregenomic and mRNAs are generated after removing the junction sequences of their corresponding primary transcripts. Production of HBV proteins and virions is expected to be the same as in natural HBV infection, but these HBV virions do not infect mouse hepatocytes.

FIG. 2A shows serum HBV titers measured by real-time PCR (detection limit $5 \times 10^3$ copies/ml) at one week after AAV injection. The values are expressed as the mean±s.d. FIG. 2B shows that electron microscopic analysis revealed the presence of infectious HBV Dane particles in the serum of mice receiving both AAV/5'-HBV-SD and AAV/3'-HBV-SA ($10^{12}$ vg of each vector per mouse). This AAV dosage was used in all subsequent experiments and is denoted as AAV/HBV transduction. Scale bar, 100 nm. FIG. 2C shows representative sections of the liver of mice receiving AAV/GFP or AAV/HBV stained immunohistochemically for HRc and HRs, Scale bar, 100 µm. (FIG. 2D) Mean and individual serum HBV titers in C57BL/6 (n=10), FVB (n=10), BALB/c (n=15), and ICR (n=10) mice receiving AAV/HBV: the detection limit was $5 \times 10^3$ gc/ml and all controls were negative.

In FIG. 4A, serum samples (n=4 of each group) were collected 8 weeks post AAV injection and the amounts of HBV proteins and anti-HBV antibodies measured by ELISA. In FIGS. 4B-4G, mice were sacrificed at different times (n=4 for each time point) and CD8$^+$ T lymphocytes isolated from the liver (FIGS. 4B, 4D, 4F) and spleen (FIGS. 4C, 4E, 4G) to perform the IFN-γ ELISPOT assay. CD8$^+$ T cells were cultured for 18-24 h with target cells (EL4, H-2$^b$) pulsed with HBs190 and HBs208 or the control OVA peptide, then were subjected to IFN-γ analysis. Additional controls were no peptide (negative) and concanavalin A stimulation (positive). Representative photographs of spots at week 2 (FIGS. 4B and 4C) and the summary of the quantitative results (mean±s.d.) (FIGS. 4D and FIG. 4E) for the intrahepatic (FIGS. 4B, 4D) and splenic (FIGS. 4C, 4E) lymphocytes are presented. The kinetics for the IFN-γ ELISPOT results from week 1 to week 8 post AAV transduction are presented for intrahepatic (FIG. 4F) and splenic (FIG. 4G) lymphocytes. Experiments were performed three times with similar results.

FIGS. 6A-6D are paraffin-embedded liver sections stained with hematoxylin and eosin. FIGS. 6A, 6B are micrographs of representative liver sections from AAV/GFP-transduced (FIG. 6A) and AAV/HBV-transduced (FIG. 6B) mice. Images of selected regions from (FIG. 6A) and (FIG. 6B) are shown at high power in (FIG. 6C) and (FIG. 6D), respectively. Inflammatory infiltration and mitotic cells are marked, respectively, by arrowheads and arrows. FIGS. 6E and 6F are Immunohistochemical stained micrographs showing more PCNA positive cells in AAV/HBV-transduced mice (FIG. 6F) than in AAV/GFP-transduced mice (FIG. 6E). PCNA-positive nuclei are stained dark red (arrowhead). FIGS. 6G-6I show results of quantitative analysis of the labeling index for inflammatory infiltration (FIG. 6G) and for mitotic cells (FIG. 6H) from a total of 22 images at 100× magnification and for PCNA-positive cells (FIG. 6I) from a total of 25 images at 100× magnification. The results are presented as the mean±s.d. Scale bars, 1 mm (FIGS. 6A, 6B). Scale bars, 100 μm (FIGS. 6C-6F).

In FIG. 7A, H&E staining showed that a liver section from a representative C57BL/6 mouse at 6 months after AAV/HBV transduction displays an acidophilic intranuclear inclusion body, which resulted in nucleus enlargement (arrows). lmmunohistochemical staining showed nuclear expression of HBc (FIG. 7B) and cytoplasmic expression of HBs (arrows) (FIG. 7C) in hepatocytes. In FIG. 7D, the 'ground glass' appearance of cytoplasmic HBs is confirmed by Orcein staining (arrow). Scale bars, 200 μm (FIGS. 7A-7C). Scale bars, 100 μm (FIG. 7D).

FIG. 8C shows HBc expression in the liver (left panel) and kidney (right panel) detected by immunohistochemical staining. Scale bar, 200 μm.

FIGS. 9A-9C show gross appearance (FIG. 9A) and histological features (FIGS. 9B-9C) of liver tumors from one representative mouse (IF1123, 13 months after HBV transduction). The tumors displayed a distinctive "nodule-in-nodule" appearance (FIG. 9B), in which a moderately to poorly differentiated HCC (T1) with a thick trabecular pattern (FIG. 9C) developed within a well differentiated HCC (T2). The arrows indicate the border of the tumor. FIGS. 9D-9H show other histological features of the liver lesions, including a pseudoglandular pattern of hepatic plates (FIG. 9D), increased cellularity and nuclear atypia (FIG. 9E, arrow), absence of portal tracks in the tumor lesions (FIG. 9F), portal invasion by atypical hepatocytes (FIG. 9G, arrows), and intra-cytoplasmic pale bodies (FIG. 9H). In FIG. 9H, the insets under higher magnification show H&E staining (top) and fibrinogen immunostaining of the pale bodies (bottom). Scale bar, 1 cm (FIG. 9A). Scale bars, 1 mm (FIGS. 9B, 9F, 9H). Scale bars, 100 μm (FIGS. 9C-9E, 9G, insets 9H).

FIGS. 10A-10C show H&E staining of the non-tumor liver tissues from one representative AAV/HBV-transduced mouse with HCC. The sections show portal (FIG. 10A) and parenchymal (FIG. 10B) mononuclear cell infiltration with focal necrosis and acidophilic bodies scattered across the sections. Pronounced steatosis (FIG. 10C) was commonly observed. In FIG. 10D, sirius red staining reveals bridging fibrosis in the parenchyma and surrounding the tumor nodules.

DETAILED DESCRIPTION OF THE INVENTION

Definitions

Figure 1:
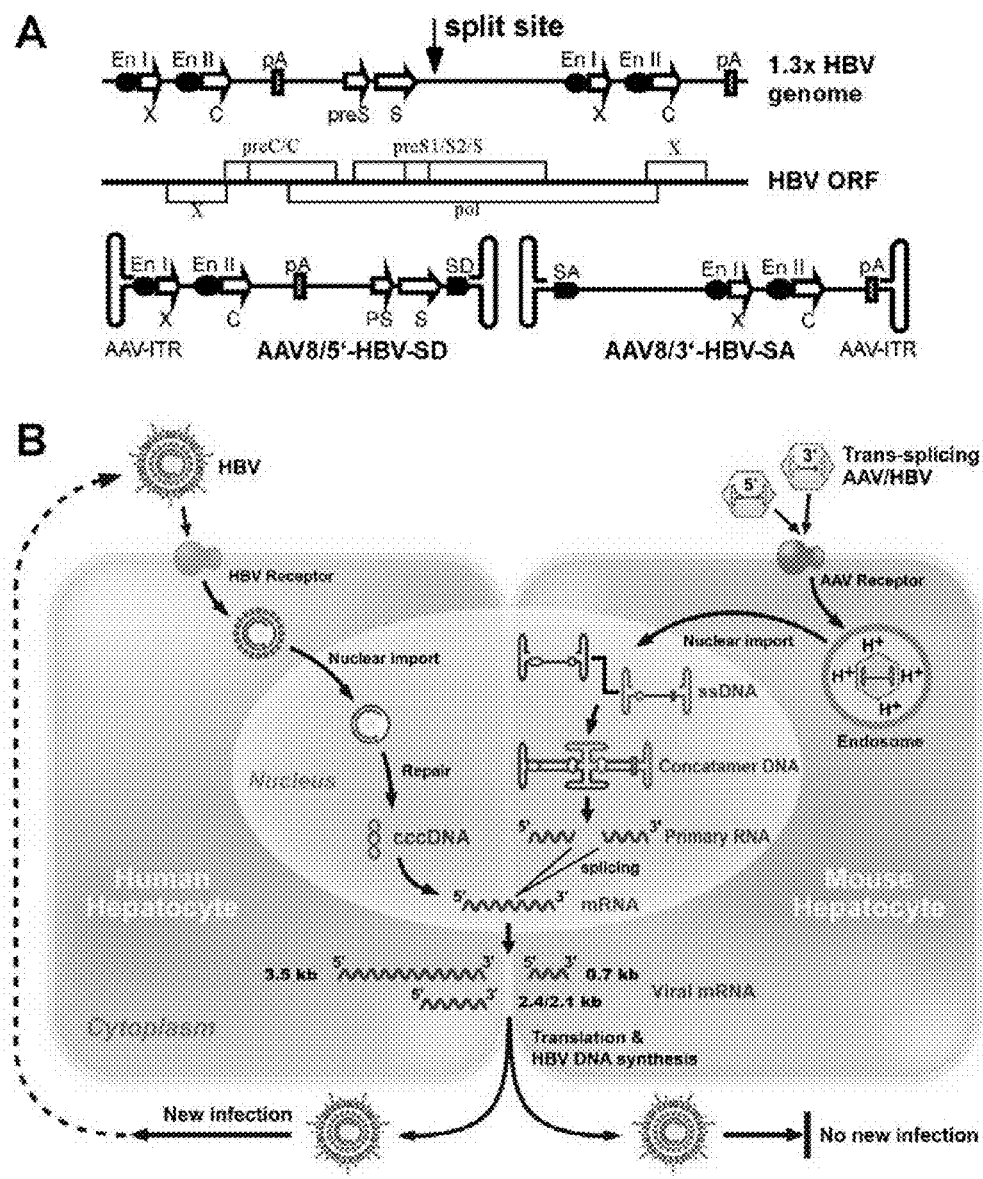
FIG. 1 shows HBV transduction of mouse hepatocytes using trans-splicing AAV vectors.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The invention relates to the discovery of successful transduction of hepatitis B virus (HBV) into immunocompotent mice using the adeno-associated virus (AAV) trans-splicing technique. (Lai et al., (2006) "Synthetic intron improves transduction efficiency of trans-splicing adeno-associated viral vectors" Hum Gene Ther 17, 1036-1042; Lai et al., (2005) "Efficient in vivo gene expression by trans-splicing adeno-associated viral vectors" *Nat Biotechnol* 23, 1435-1439.) These AAV/HBV-transduced mice showed not only persistent HBV DNA and protein expression, but also HBV-specific T cells that were especially enriched in the liver, resulting in hepatic inflammation and regeneration and the eventual development of HCC. The AAV/HBV-induced hepatocellular carcinoma (HCC) model will be useful in studying the immunopathogenic mechanism of HBV chronic diseases and in developing new treatment strategies for HCC.

The trans-splicing technique, i.e. using two AAV vectors, as aforementioned was used for the reason of safety concern. In fact, one AAV vector could have been used to carry the whole HBV genome, which presumably would have a better transduction effect.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Construction and production of AAV vectors. Plasmid pHBV1.3 (FIG. 1A), containing the 1.3-times overlength HBV genome (genotype D), was split at the CAG/G site between nucleotides 2192 and 2193, and a highly conserved synthetic intron inserted by PCR (Lai et al. (2006) "Synthetic intron improves transduction efficiency of trans-splicing adeno-associated viral vectors" *Hum Gene Ther* 17, 1036-1042). The primer pairs for the 5'-HBV donor fragment (2214 bp) and 3'-HBV acceptor fragment (1976 bp) were 5'-AAAAAGCTTATGTAT-TCAATCTAAGCAG-3' (SEQ ID NO: 1), 5'-TTTCTC-GAGTATTGGTCTCCTTAAACCTGTCTTG-TAACCTTGATACTTACCTGA ACTGGAGCCACCAGC-3' (SEQ ID NO: 2), and 5'-AAAGAATTCCTCTTGCGTTTCTGATAG-GCACCTATTGGTCTTACTGACATCCA CTTTGC-CTTTCTCTCCACAGGAACAGTAAACCCTGTTCTG-3' (SEQ ID NO: 3), 5'-TTTGTCGACTACTGAAGGAAAGAAGTCAG-3' (SEQ ID NO: 4). The reverse primer for the donor HBV fragment contains the intronic donor sequence from the first intron in the human β-globulin gene, while the forward primer for the acceptor HBV fragment contains the intronic acceptor sequences from the human immunoglobulin heavy chain gene. These two PCR products were subcloned into the pAAV-MCS vector (Stratagene), which contains the inverted terminal repeat of AAV serotype 2 at both ends, to generate plasmids pAAV5'-HBV-SD and pAAV-3'-HBV-SA. The pAAV-GFP plasmid expressing green fluorescent protein (GFP) was a gift from Dr. Jin-Jer Cheng (Academia Sinica, Taipei, Taiwan). Pseudotyped AAV8 vectors carrying the 5'-HBV-SD, 3'-HBV-SA, or GFP coding sequence were generated by the triple transfection method and purified by CsCl sedimentation. The control AAV8/GL2 vector encoding a small hairpin RNA targeting the firefly luciferase transcript has been described previously. The physical vector titers were assessed by quantitative PCR. It is noteworthy that the trans-splicing technique is important for carrying vinises with a viral genome greater than 5 kb, such as hepatitis C virus. However, for hepatitis B virus study the trans-splicing technique is not necessary scientifically. The only reason for using trans-splicing technique in this study was to follow the request of the institutional regulations.

Animals. The BALB/c, C57BL/6, and FVB mice were purchased from the National Laboratory Animal Breeding and Research Center (Taipei, Taiwan). The ICR mice were purchased from BioLASCO (Ilan, Taiwan). The C57BL/6/HBV transgenic mouse line was obtained by backcrossing ICR/HBV transgenic mice containing the 1.3× HBV genome for more than 10 generations onto the C57BL/6 genetic background. All animals were housed in a specific pathogen-free environment in the animal facilities of the Institute of Biomedical Sciences, Academia Sinica. All experimental procedures were in compliance with the Academia Sinica IACUS and Council of Agriculture Guidebook for the Care and Use of Laboratory Animals.

AAV injections. All mice were injected i.v. at 6 to 8 weeks of age with the indicated titer of both AAV/5'-HBV-SD and AAV/3'-HBV-SA (AAV/HBV). Mice injected with AAV/GFP or AAV/GL2 were used as negative controls. Sera and tissue samples were collected at different times post AAV injection.

PCR. For HBV quantification, serum HBV DNA was extracted using the QuickGene-810 automated Nucleic Acid Isolation System (FUJIFILM, Japan) and quantified by a sensitive hybridization probe-based real-time PCR. The PCR primer pairs for HBV DNA were 5'-CTCCAC-CAATCGCCAGTC-3' (SEQ ID NO: 5) and 5'-ATCCTC-GAGAAGATTGACGATAAT-3' (SEQ ID NO: 6). The 3'-fluorescein labeled donor and 5'-Red640-labeled acceptor probes were 5'-CATGGCCTGAGGATGAGT-GTTTCT CA-3' (SEQ ID NO: 7) and 5'-AGGTGGAGA-CAGCGGGGTAGG-3' (SEQ ID NO: 8) (LightCycler FastStart, Roche Diagnostics). Plasmid pHBV1.3 was prepared at 10-fold dilutions ($1.33 \times 10^3$ to $1.33 \times 10^9$ copies/ml) to generate a standard curve in parallel PCR reactions.

Serological analysis. Serological markers for HBV (HBs, HBe, anti-HBs, anti-HBe and anti-HBc) were quantified using an Elecsys Systems electrochemiluminescence kit and a Cobas e analyzer (Roche Diagnostics GmbH).

Electron microscopy. Particles in serum samples were concentrated on a 10% sucrose gradient by ultracentrifugation at 287,730 g at 4° C. for 12 h. The concentrated pellet was resuspended in 50 mM Tris-150 mM NaCl, pH 7.4 buffer, negatively stained with 2% uranyl acetate on a carbon-coated grid, and examined by transmission electron microscopy using a Tecnai G2 Spirit TWIN (FEI Company, USA) operating at 75 kV.

IFN-γ ELISPOT assays. At the indicated experimental time point, splenocytes and intrahepatic lymphocytes (IHLs) were isolated from the AAV/HBV- and AAV/GFP-injected mice for IFN-γ ELISPOT assays. A mouse IFN-γ ELISPOT Ready-Set-Go kit (eBioscience) was used according to the manufacturer's instructions. Briefly, CD8$^+$ T cells ($4 \times 10^5$-$2 \times 10^5$ per well), positively selected from IHLs and splenocytes using mouse CD8a Micro-Beads (Miltenyi Biotec), were cultured with EL-4 cells pulsed with 10 µg/ml of peptides on MultiScreen-IP plates (Millipore) precoated with anti-IFN-γ capture antibody. Three H-2K$^b$-restricted HBV epitopes, HBs190 and HBs208 located in the envelope and HBc93 in HBc, were used in this assay. The negative controls were OVA257 peptide, a H2-K$^b$-restricted ovalbumin epitope, and no peptide and the positive control was concanavalin A stimulation (4 μg/ml). Spots were developed 18-24 h later with biotinylated antibody against IFN-γ, followed by streptavidin-horseradish peroxidase, then 3-amino-9-ethylcarbazole (AEC) substrates, and were counted using an AID ELISPOT Reader System with software 5.0 (AID Gm bH).

Histology and immunohistochemistry. Formaldehyde-fixed and paraffin-embedded liver tissues were sectioned at 5 μm, mounted, heat-fixed onto glass slides, and subjected to hematoxylin-eosin (H&E) staining for general histological inspection, Sirius Red staining for collagen fiber analysis, and Orcein staining for analysis of intracytoplasmic inclusion bodies which reflect HBs deposition. For immunohistochemical staining, tissue sections were deparaffinized, soaked in target retrieval solution (TRS, pH 6.1, DAKO), and irradiated (500 W) in a microwave oven for 15 min. The tissue sections were then treated with 3% hydrogen peroxide to block any endogenous peroxidase, and blocked with M.O.M. mouse immunoglobulin blocking reagent (Vector Laboratories). The primary antibodies used were mouse anti-HBs (clone 3E7), rabbit anti-HBc, rabbit anti-fibrinogen, and mouse anti-PCNA (clone PC10) (all from DAKO). The sections were then washed and incubated with the corresponding horseradish peroxidase-conjugated secondary antibodies. After thorough washing, the sections were immersed in DAB (Sigma-Aldrich) or AEC (Sigma-Aldrich) and counterstained with hematoxylin. For quantitative analysis of the inflammatory, mitotic, and PCNA indices, 22-25 images per slide were randomly taken at 100-fold magnification, visualized using a ScanScope CS Digital Slide Scanner (Aperio Technologies Inc), and analyzed using the ImageScope program.

Statistics. All data were analyzed for significance by the Student's t test. A p value of <0.05 was considered significant.

Results

HBV Production by Trans-Splicing AAV Vectors

Since mouse hepatocytes are known to support HBV replication, the failure of HBV infection in mice is presumed to be due to a lack of HBV receptors on mouse hepatocytes. To bypass this entry step of HBV infection, we used the hepatotropic AAV serotype 8 vector (AAV8) to introduce the HBV genome into mouse hepatocytes. To increase operation safety, we applied the AAV trans-splicing technique to generate two independent AAV vectors, AAV/5'-HBV-SD and AAV/3'-HBV-SA, each carrying approximately half of the HBV genome flanked by donor or acceptor splice sequences (FIG. 1A). We hypothesized that coadministration of these two vectors would generate functional HBV pregenomic and messenger RNAs after head-to-tail intermolecular concatamerization and productive transcription and splicing of the reconstituted HBV genome (FIG. 1B).

Figure 2:
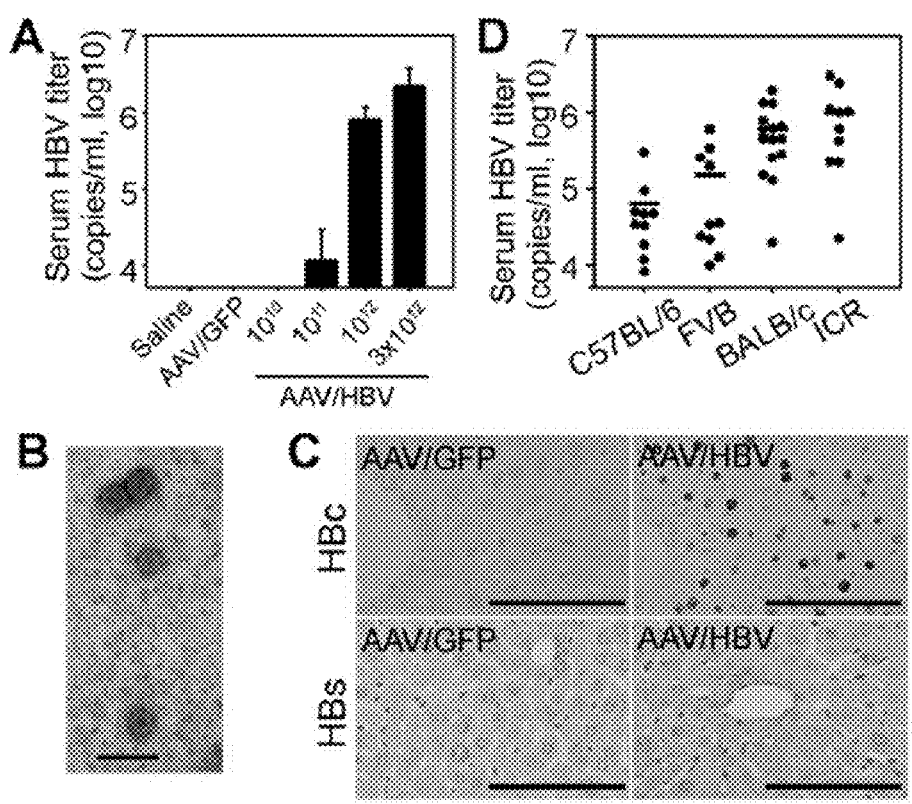
FIG. 2 shows co-injection of mice with trans-splicing AAV vectors produces HBV virions and proteins. BALB/c mice (n=5) were injected i.v. with saline, AAV/GFP ($2 \times 10^{12}$ vg per mouse), or equal doses of both AAV/5'-HBV-SD and AAV/3'-HBV-SA (between $10^{10}$ and $3 \times 10^{12}$ vg of each per mouse).
Figure 3:
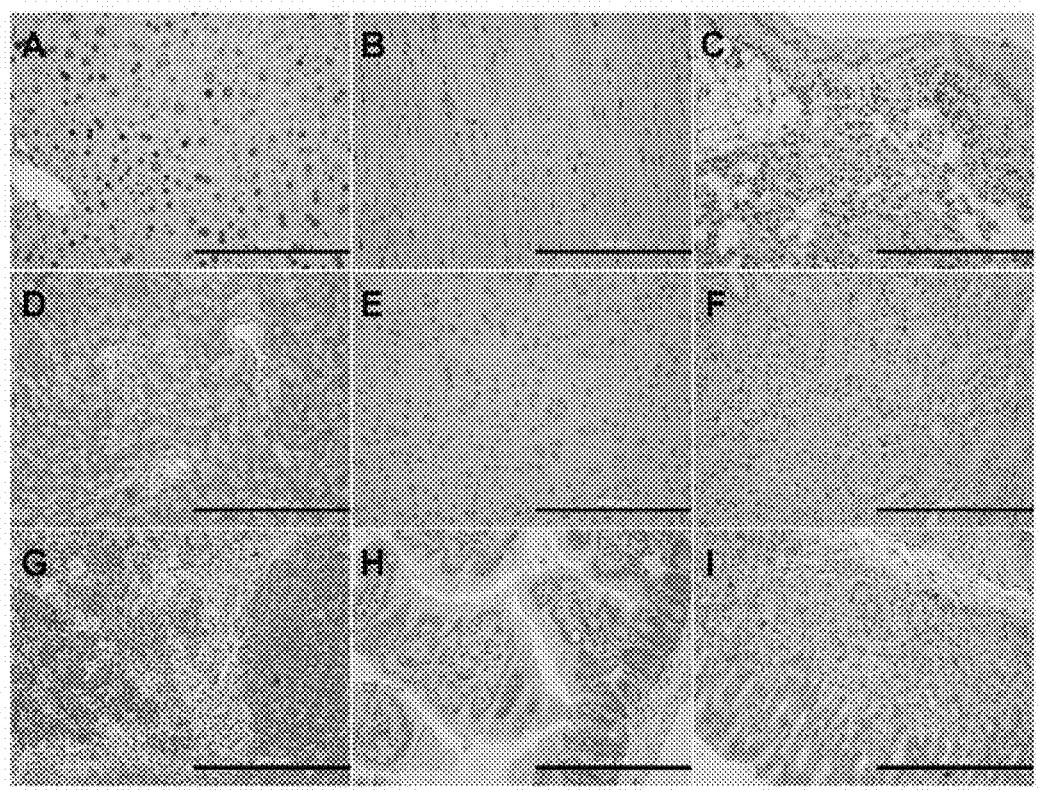
FIG. 3 shows HBc expression in the liver (FIG. 3A), but no HBc expression in the heart (FIG. 3B), lung (FIG. 3C), brain (FIG. 3D), pancreas (FIG. 3E), kidney (FIG. 3F), spleen (FIG. 3G), stomach (FIG. 3H), and intestine (FIG. 3I) of the AAV/HBV-transduced BALB/c mice of FIG. 2A. Scale bar, 200 µm.

Male BALB/c mice (6- to 8-weeks-old) co-injected intravenously (i. v.) with equal amounts of AAV/5'-HBV-SD and AAV/3'-HBV-SA (denoted hereafter AAV/HBV) ranging from $10^{10}$ to $3 \times 10^{12}$ vector genomes (vg) of each vector per mouse (5 mice per dose) produced HBV DNA in the serum in a dose-dependent manner (FIG. 2A) and electron microscopy demonstrated the presence of infectious Dane particles in the serum (FIG. 2B). In contrast, mice injected with saline or control AAV8 vector expressing green fluorescent protein (AAV/GFP) at the dose of $2 \times 10^{12}$ vg per mouse did not produce detectable HBV DNA in the serum. Immunohistochemical analysis of liver tissues revealed that HBV core (HBc) and envelope (HBs) proteins were expressed in mice injected with the AAV/HBV vectors, but not in mice transduced with AAV/GFP; the data for the $10^{12}$ vg group are shown in FIG. 2C, but similar results were obtained in all groups. The dose of $10^{12}$ vg was used in all subsequent experiments. HBV protein expression was seen in the liver, but not in the other eight organs examined (FIG. 3), reflecting the liver tropism characteristic of HBV and AAV8 vectors. Since the split site was located within the HBV preS1/S2/S and polymerase open reading frames (FIG. 1A), our results suggest that the head-to-tail intermolecular recombination of the AAV genome occurred in the co-transduced hepatocytes and led to production of fully functional HBV genomes and proteins.

To examine whether the genetic background affected HBV production by AAV-mediated HBV infection, three inbred strains (C57BL/6 [n=10], FVB [n=10], and BALB/c [n=15]) and one outbred strain (ICR [n=10]) of mice were injected i.v. with AAV/HBV. All mice used in this experiment were male. Significantly, every mouse of the four different mouse strains became HBV-positive 4 weeks after injection with AAV/HBV (FIG. 2D). The BALB/c and ICR mice produced higher levels of serum HBV (mean titer $6.1 \times 10^5$ and $1.0 \times 10^6$ genome copies [gc] per ml, respectively) than the C57BL/6 and FVB mice (mean titer $6.6 \times 10^4$ and $1.5 \times 10^5$ gc per ml, respectively).

HBV Serological and Immunological Responses Induced by AAV/HBV Transduction

Figure 4:
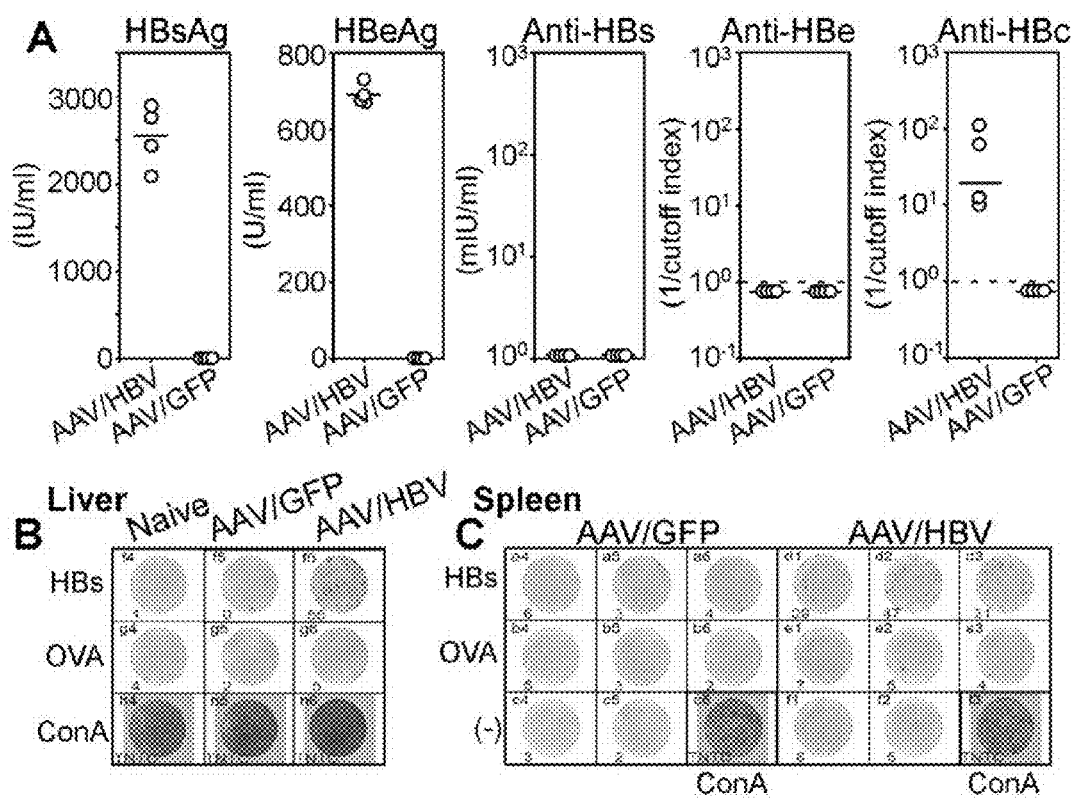
FIG. 4 shows HBV serological and immunological responses induced by AAV/HBV transduction. C57BL/6 mice (H2$^b$ haplotype) were injected i.v. with AAV/HBV or AAV/GFP as described above.
Figure 4:
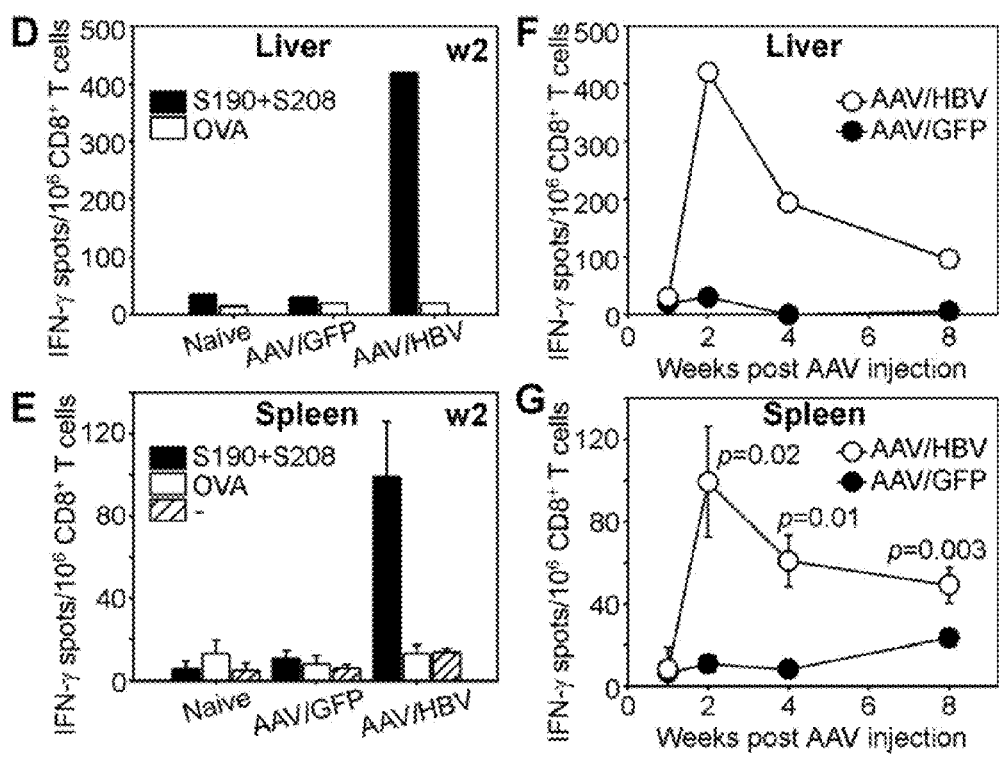

We then examined virological and immunological features following AAV/HBV transduction. All subsequent experiments were performed on C57BL/6 mice because this mouse strain is commonly used to produce genetically engineered mice with selective immune deficiency, which are important for our ongoing mechanistic studies on the immunopathogenesis of this animal model. Mice were given one i.v. injection of AAV/HBV (n=4) or AAV/GFP (n=4), then serum samples were collected 8 weeks later and tested for HBV proteins and HBV-specific antibodies. Significant amounts of HBs (mean titer 2541 IU/ml) and hepatitis B e antigen (HBe, mean titer 691 U/ml) were detected in mice transduced with AAV/HBV, but not the control AAV/GFP (FIG. 4A). The AAV/HBV-transduced mice were negative for anti-HBs and anti-HBe antibodies, but positive for anti-HBc antibody (FIG. 4A). This profile of HBV serological markers in AAV/HBV-transduced mice is similar to that observed in chronic hepatitis B patients and was maintained for at least 16 months following AAV/HBV-transduction (see Table 1).

TABLE 1

| Strain | Mouse ID | AAV | Months post-injection months | HBsAg IU/mL | HBeAg U/mL | ALT U/L | Liver tumors | No. of visible tumors | Largest tumor mm | Tumor Histology |
|---|---|---|---|---|---|---|---|---|---|---|
| C57BL/6 | IF1294 | AAV/HBV | 12 | 744 (+) | 421 (+) | 146 | + | 1 | 16 | HCC |
|  | IF1121 | AAV/HBV | 13 | 3324 (+) | ND | 225 | + | 2 | 22 | HCC |
|  | IF1123 | AAV/HBV | 13 | 3617 (+) | ND | 215 | + | TMTC | 17 | HCC |
|  | IF1181 | AAV/HBV | 14 | 4432 (+) | 66 (+) | 271 | + | TMTC | 17 | HCC |

TABLE 1-continued

| Strain | Mouse ID | AAV | Months post-injection months | HBsAg IU/mL | HBeAg U/mL | ALT U/L | Liver tumors | No. of visible tumors | Largest tumor mm | Tumor Histology |
|---|---|---|---|---|---|---|---|---|---|---|
| | IF1182 | AAV/HBV | 14 | 770 (+) | 623 (+) | 103 | + | 3 | 4 | Dysplastic nodules |
| | IF1252 | AAV/HBV | 16 | 1964 (+) | 202 (+) | 345 | + | TMTC | 16 | HCC |
| | IF1253 | AAV/HBV | 16 | 1662 (+) | 37 (+) | 266 | + | TMTC | 23 | HCC |
| | IF1254 | AAV/HBV | 16 | 4766 (+) | 32 (+) | 369 | + | TMTC | 23 | HCC |
| | IF1258 | AAV/HBV | 16 | 2912 (+) | 21 (+) | 370 | + | TMTC | 20 | HCC |
| | IF1259 | AAV/HBV | 16 | 2753 (+) | 175 (+) | 350 | + | 2 | 23 | HCC |
| | IF1260 | AAV/HBV | 16 | 2318 (+) | 54 (+) | 76 | + | ND | ND | Dysplastic nodules |
| | IF1261 | AAV/HBV | 16 | 1928 (+) | 76 (+) | 443 | + | TMTC | ND | HCC |
| C57BL/6/HBVtg | IF1225 | AAV/GL2 | 13 | 4325 (+) | 712 (+) | ND | − | − | − | − |
| | IF1235 | AAV/GL2 | 13 | 2483 (+) | 587 (+) | 98 | − | − | − | − |
| | IF1237 | AAV/GL2 | 13 | 2864 (+) | 639 (+) | 66 | − | − | − | − |
| | IF1421 | AAV/GL2 | 15 | 864 (+) | ND | 47 | − | − | − | − |
| | IF1226 | AAV/GL2 | 16 | 3015 (+) | 516 (+) | 71 | − | − | − | − |
| | IF1227 | AAV/GL2 | 16 | 591 (+) | 996 (+) | 63 | − | − | − | − |
| | IF1420 | AAV/GL2 | 15 | 1534 (+) | ND | 19 | − | − | − | − |
| | IF1422 | AAV/GL2 | 15 | 908 (+) | ND | 80 | − | − | − | − |
| | IF1241 | AAV/GL2 | 16 | 1546 (+) | 325 (+) | 19 | − | − | − | − |
| | IF1239 | AAV/GL2 | 16 | 680 (+) | 874 (+) | 40 | − | − | − | − |
| | IF1240 | AAV/GL2 | 16 | 2135 (+) | 525 (+) | 110 | − | − | − | − |
| | IF1419 | AAV/GL2 | 19.5 | 1413 (+) | ND | 23 | − | − | − | − |
| | IF1417 | AAV/GL2 | 19.5 | 3552 (+) | ND | 25 | − | − | − | − |

Abbreviation: ND, not determined; TMTC, too many to count

Since CD8+ T lymphocytes are considered to be the main effector cells in viral control and liver damage during chronic hepatitis B infection, we investigated the dynamics of HBV-specific CD8+ T cell responses following AAV/HBV transduction. C57BL/6 mice, a mouse strain with the major histocompatibility complex H-$2^b$ haplotype, were injected i.v. with AAV/HBV or AAV/GFP, then intrahepatic and splenic CD8+ T lymphocytes were isolated at different times (n=4 for each time point) and analyzed for their responses to three known H-2K$^b$-restricted epitopes, two located in HBs (HBs190, HBs208) and one in HBc (HBc93), using the IFN-γ ELISPOT assay. AAV/HBV transduction did not induce detectable HBs-specific (tested with a combination of HBs190 and HBs208) or HBc-specific CD8+ T cells at one week after transduction, but at week 2, significant numbers of HBs-specific CD8+ T cells were observed in the liver (FIGS. 4B, 4D) and, to a lesser extent, in the spleen (FIGS. 4C, 4E), then the number of HBs-reacting CD8+ T cells in both the liver (FIG. 4F) and spleen (FIG. 4G) decreased with time. CD8+ T cells from AAV/HBV-transduced mice were unresponsive to the HBc93 epitope or an irrelevant H2-K$^b$-restricted ovalbumin epitope (OVA257) over the 8-week observation period. The control AAV/GFP transduction did not induce detectable CD8+ T cell responses to any of the peptides.

Hepatocellular Carcinoma is Induced in AAV/HBV-Transduced Mice

Figure 5:
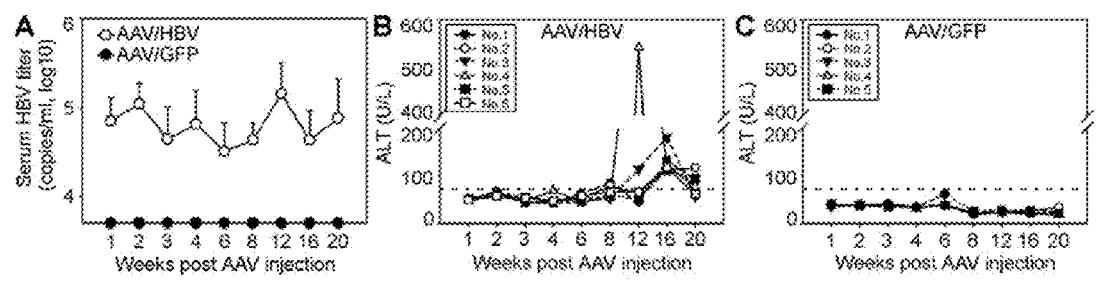
FIG. 5 shows kinetics of serum HBV titers and alanine aminotransferase (ALT) activity after AAV/HBV transduction. C57BL/6 mice were injected with AAV/HBV (n=6) or AAV/GFP (n=5) as described above, then average serum HBV titers (mean±s.d.) (FIG. 5A) and the ALT values for individual subjects (FIG. 5B, 5C) were measured over time. The dashed line represents twice the mean ALT value in wild-type untreated C57BL/6 mice (n=6).

We then investigated the long-term pathological consequences of persistent HBV expression in immunocompetent hosts. C57BL/6 mice were injected i.v. with AAV/HBV (n=6) or AAV/GFP (n=5) as described above. Throughout the 20-week observation period, the AAV/HBV-transduced mice produced relatively stable levels of serum HBV, with a mean titer between $3 \times 10^4$ to $2 \times 10^5$ gc per nil (FIG. 5A). Serum ALT levels in AAV/HBV-transduced mice were normal up to week 8, but elevated (more than twice the mean ALT value in wild-type untreated mice, shown by the dashed horizontal line) at 12-20 weeks (FIG. 5B), suggesting accumulation of liver injury with time in these mice. In contrast, the control AAV/GFP mice displayed normal ALT levels at all times (FIG. 5C).

Figure 6:
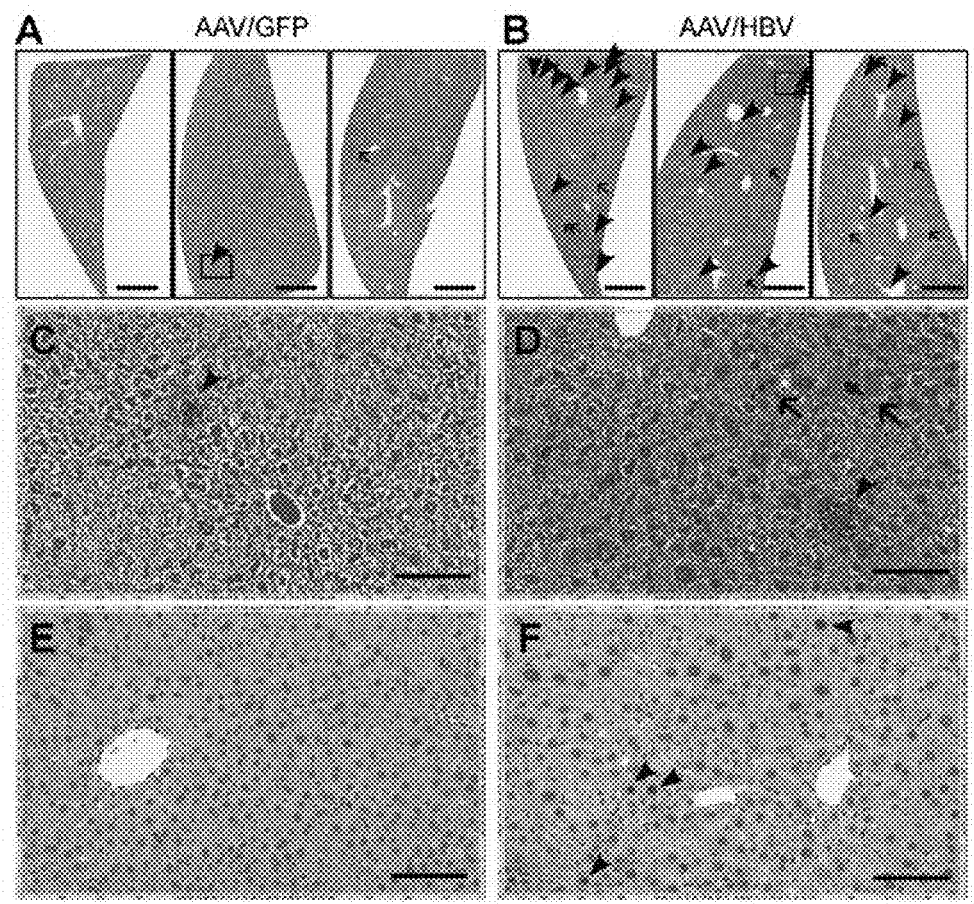
FIG. 6 shows histological changes after AAV/HBV transduction. The mice of FIG. 4 were sacrificed 6 months after AAV transduction and their livers removed for histopathological analysis.
Figure 6:
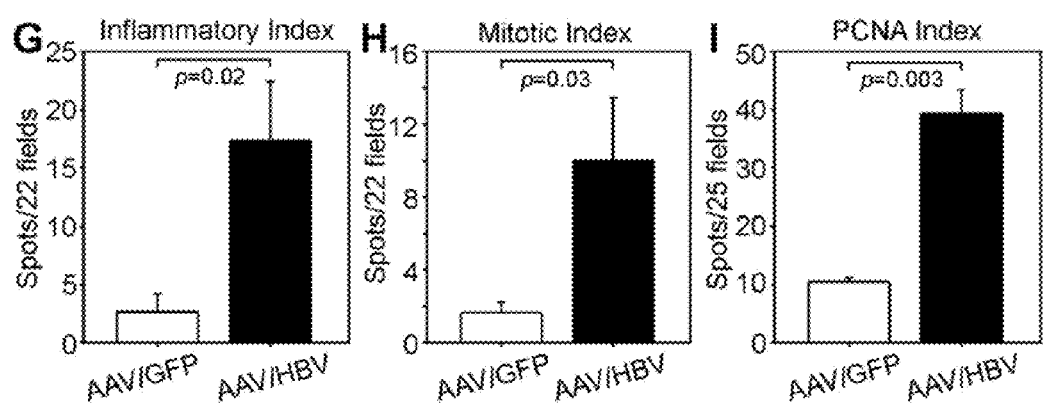
Figure 7:
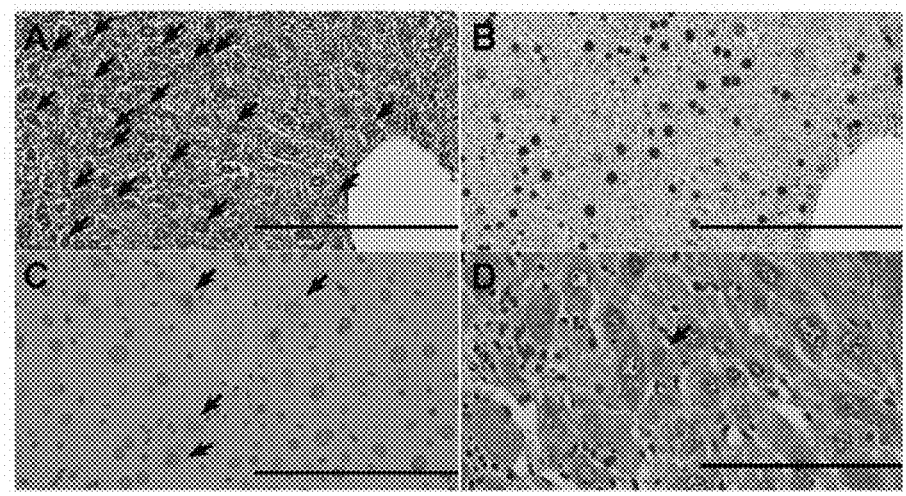
FIG. 7 shows persistent HBs and HBc expression in the liver after AAV/HBV transduction.

Consistent with the ALT results, no significant histological changes were observed in the liver of AAV/HBV- or AAV/GFP-transduced mice at 8 weeks and 3 months after AAV transduction (data not shown). Six months after transduction, we observed much more highly pronounced liver histological changes (inflammatory infiltration and mitosis) in the AAV/HBV group (FIGS. 6B, 6D) than in the AAV/GFP group (FIGS. 6A, 6C). Semiquantitative analysis revealed that the average number of inflammatory infiltrations counted microscopically in the liver of the AAV/HBV-transduced mice was significantly higher than that in mice transduced with AAV/GFP (17.3±5.1 vs. 2.7±1.5, p=0.02), as was the number of mitotic cells (10.0±3.5 vs. 1.7±0.6, p=0.03) (FIGS. 6G, 6H). The liver in the AAV/HBV-transduced mice also contained a significantly higher number of hepatocytes expressing the cell proliferating marker proliferating cell nuclear antigen (PCNA) than the AAV/GFP-transduced mice (39.3±4.0 vs. 10.5±0.7, p=0.003, FIGS. 6E, 6F, 6I). In AAV/HBV-transduced mice, acidophilic nuclear inclusions were commonly observed that pushed the nucleoli aside and resulted in enlargement of the nucleus (FIG. 7A). Immunohistochemical analysis revealed that these cells were positively stained for HBc (FIG. 7B). A smaller number of hepatocytes also expressed cytoplasmic HBs, as shown by immunohistochemical and Orcein staining (FIGS. 7C, D). These data suggest that persistent HBV expression in AAV/HBV mice causes liver injury, which promotes subsequent hepatocyte regeneration.

Figure 8:
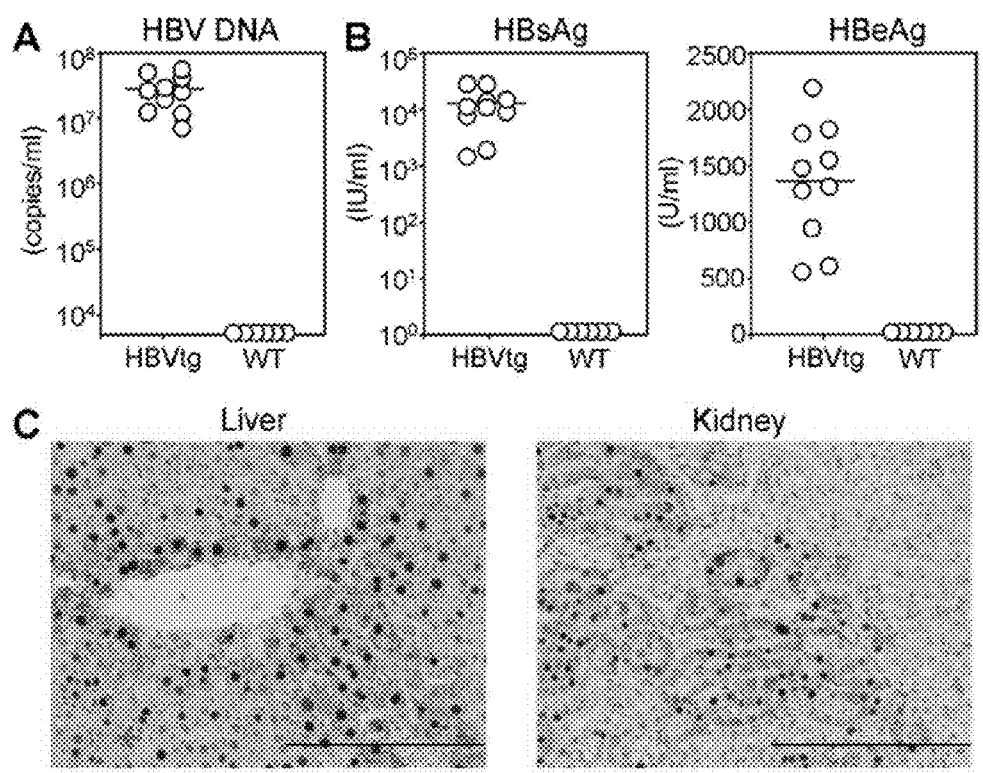
FIG. 8 shows HBV gene expression in C57BL/6/HBV transgenic mice. C57/BL/6/HBV transgenic mice (n=10) and wild-type C57BL/6 mice (n=6) at 8 weeks of age were analyzed for serum HBV DNA by real-time PCR (FIG. 8A) and HBV proteins (HBs and HBe) by ELISA (FIG. 8B).

To investigate whether persistent HBV expression in immunocompetent mice led to development of HCC, C57BL/6 mice (n=12) were injected i.v. with AAV/HBV and their livers removed at 12-16 months after injection for macroscopic and histopathological analysis. To evaluate the contribution of anti-HBV immunity to HCC development, C57BL/6/HBV transgenic mice (n=13), which are centrally immunotolerant to HBV, were injected i.v. with the same amount of a control AAV8 vector (AAV/GL2), encoding a small hairpin RNA targeting luciferase transcript; these HBV transgenic mice produced high titers of HBV DNA (FIG. 8A) and proteins (HBs and HBc, FIG. 8B) in the scrum and were positively stained for HBc in the liver and kidney (FIG. 8C).

Figure 10:
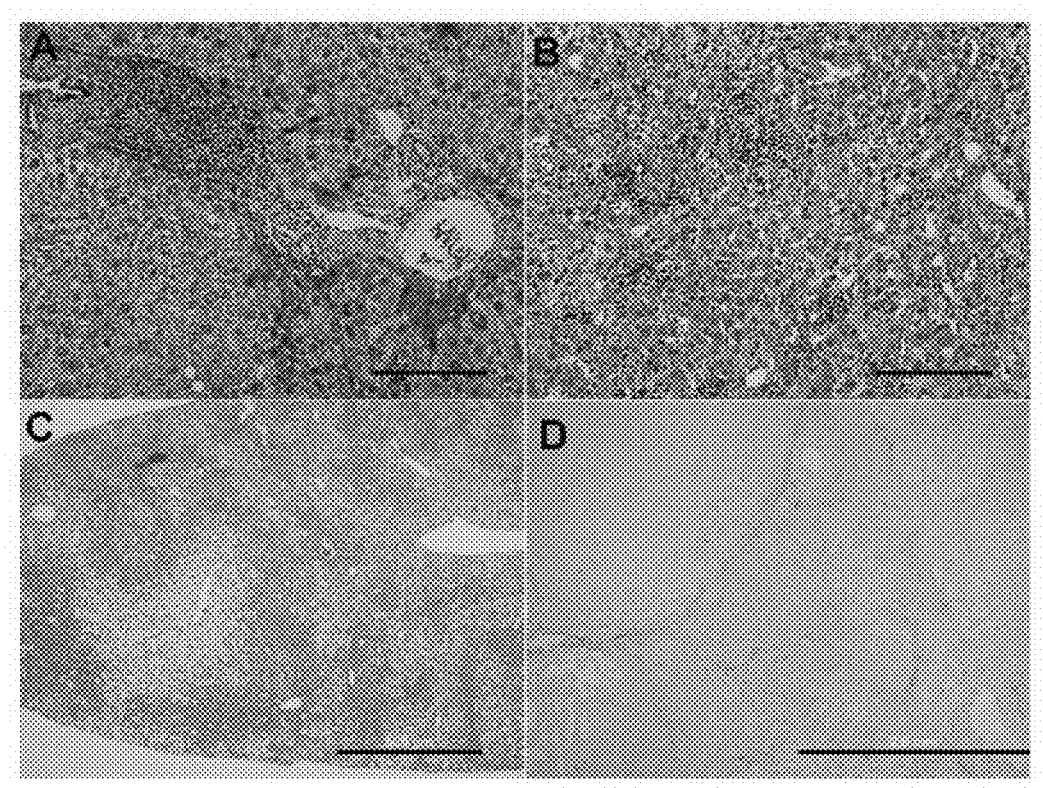
FIG. 10 shows histological changes in the adjacent non-tumor liver tissues in AAV/HBV-transduced mice.
Figure 11:
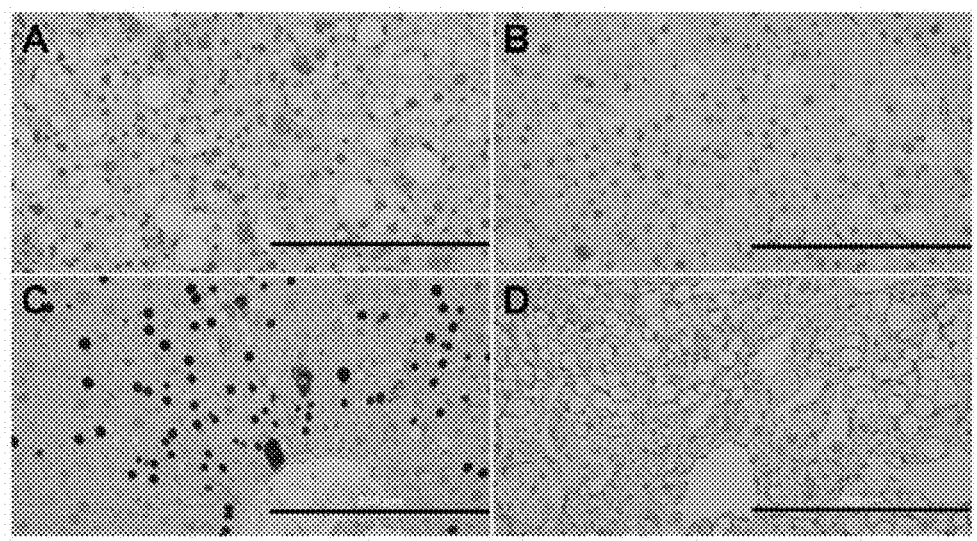
FIG. 11 shows HBV protein expression is lost in AAV/HBV-induced HCC. Immunohistochemical staining of the liver sections from a representative AAV/HBV-transduced mice with HCC (IF1121) showing that HBs (FIGS. 11A, 11B) and HBc (FIGS. 11C, 11D) are expressed in the adjacent non-tumor tissue (FIGS. 11A, 11C), but not in the tumor (FIGS. 11B, 11D). HBs expression is located in the cytoplasm, while HBcAg is found mainly in the nucleus, but also in the cytoplasm of a few hepatocytes near the central vein. Scale bars, 200 μm.

All the AAV/HBV-transduced mice (12 of 12, 100%) developed macroscopically visible liver tumor nodules between 12 and 16 months after AAV/HBV transduction (Table 1). FIG. 9A shows an example of the multiple well-vascularized tumors (mouse IF1123, 13 months after AAV/HBV transduction). Microscopic examination revealed that these tumors had a distinctive "nodule-in-nodule" appearance (FIG. 9B), in which a poorly or moderately differentiated HCC, characterized by a pseudoglandular to thick trabecular pattern (T1 region, FIG. 9C), developed within a well differentiated HCC (T2 region). Other large tumors (>10 mm in diameter) were also diagnosed as moderately to well differentiated HCC, characterized by a pseudoglandular pattern (FIG. 9D), increased cellularity and nuclear atypia (FIG. 9E), the absence of portal tracts (FIG. 9F), and occasional portal invasion by atypical hepatocytes (FIG. 9G). Round amphophilic cytoplasmic inclusions were occasionally observed in the tumor areas (FIG. 9H) and showed a strong positive immunoreaction for fibrinogen (FIG. 9H bottom inset), similar to the structure of the pale bodies found in some human HCCs. Portal and parenchymal inflammatory infiltrates with focal necrosis of multiple hepatocytes were seen through the adjacent non-tumor liver tissue (FIGS. 10A, 10B). Pronounced steatosis was a common feature in the non-tumor region (FIG. 10C), which occasionally displayed mild to moderate liver fibrosis (FIG. 10D). Immunohistochemical analysis revealed that the surrounding normal liver still displayed HBs and HBc (FIGS. 11A, 11C), but, interestingly, expression of these HBV proteins was lost in the tumor tissue (FIGS. 11B, 11D). In contrast, none of the AAV/GL2-transduced C57BL/6 HBV transgenic mice (0 of 13) developed detectable liver nodules over the 13 to 19.5 month observation period (Table 1), and their livers showed either no apparent histological changes (IF1226, 16 months after AAV/GL2 transduction, FIGS. 12A, 12B) or only mild irregular steatosis (IF1421, 15 months after AAV/GL2 transduction, FIGS. 12D, 12E). At this time, these transgenic mice still displayed significant amounts of HBs and HBe in the serum (Table 1) and of HBc in the liver (FIGS. 12C, 12F). Most of these AAV/GL-2-transduced HBV transgenic mice had scrum ALT levels within the normal range, with an average titer of 55±26, while ALT levels in the AAV/HBV-transduced mice of a similar age and bearing HCC were significantly elevated, with an average titer of 265±93 (Table 1).

Discussion

HCC is the third leading cause of cancer mortality worldwide, and chronic HBV infection is one of the major risk factors for development of this cancer. The molecular mechanisms by which HBV infection leads to hepatocarcinogenesis are not completely understood, but evidence suggests that evolution to HCC may be related to the direct effect of the transcriptional activity of HBV proteins or HBV DNA integration, as well as an indirect effect through immune-mediated hepatic inflammation, injury, and regeneration. In transgenic mouse studies, overexpression and accumulation of HBV large envelope proteins or X proteins using artificial strong promoters led to development of HCC, but the levels of viral proteins expressed in these transgenic animals greatly surpassed that in natural infection and thus may not represent the real cause of HCC. Transgenic mice containing the whole HBV genome, although producing viral proteins and HBV virions under the control of the virus's own promoters and enhancers, did not manifest pathological changes or liver tumor development in several previous studies. The lack of liver injury and of HCC development in whole HBV genome transgenic mice is probably due to immune tolerance to HBV, since adoptive transfer of HBV-specific T cells induces a high incidence of HCC in these transgenic mice. Nakamoto et al. (1998) "Immune pathogenesis of hepatocellular carcinoma" *J Exp Med* 188, 341-350.

Clinical and experimental evidence suggests that hepatocyte injury in chronic HBV infection is mainly caused by antiviral immune responses. In this regard, our AAV/HBV-transduction model is superior to previous transgenic mouse models, because our model established production of HBV virions and HBV proteins expression in the liver of an immunocompetent host, more closely mimicking natural HBV infection, while previous models are centrally tolerant to HBV from birth. Indeed, our data showed that AAV/HBV-transduction induced anti-HBc antibody and a significant number of HBs-specific IFN-γ-producing $CD8^+$ T lymphocytes (FIGS. 4B-4G), which were preferentially present in the target organ, with 2-4-fold more in the liver than in the spleen. However, even with compartmentalization of HBV-specific T cells in the liver (FIGS. 4B-4G), these T cells were not able to clear HBV from AAV/HBV-transduced hepatocytes, which showed persistent expression of HBV virions (FIGS. 2A, 2B and 4A) and HBV proteins (HBs, HBc, and HBe) (FIGS. 2C and 4A, Table 1) for more than one year, a feature similarly to findings in chronic HBV patients. Our data showed that the cellular immune response induced by AAV/HBV transduction was relatively weak (FIGS. 4B-4G) compared to that induced by HBV DNA immunization (data not shown) and likely to be impaired by the persistent presence of HBV proteins, supported by the finding that the number of HBs-specific T cells decreased rapidly with time after reaching its peak at two weeks after AAV transduction (FIGS. 4F, 4G) and T cells against other HBV proteins (HBc) were never detected. Our preliminary data showed that expression of the inhibitory receptor program death 1 (PD-1) in hepatic $CD8^+$ T cells is increased in these mice and is accompanied by increased expression of its ligand PD-L1 in the liver tissue (data not shown), suggesting that the PD-1/PD-L1 interaction might play a role in impairing the function of these HBV-specific T cells, a phenomenon also observed in chronic HBV patients. We suggest that these functionally impaired HBV-specific T cells, although unable to completely clear HBV from the liver, were responsible for triggering liver damage and hepatic regeneration, leading to progressive liver diseases. The elevated ALT levels (FIG. 5B) and the higher number of hepatocytes undergoing mitosis and expressing PCNA in AAV/HBV-transduced mice compared to AAV/GFP-transduced mice (FIG. 6) support this hypothesis.

Figure 9:
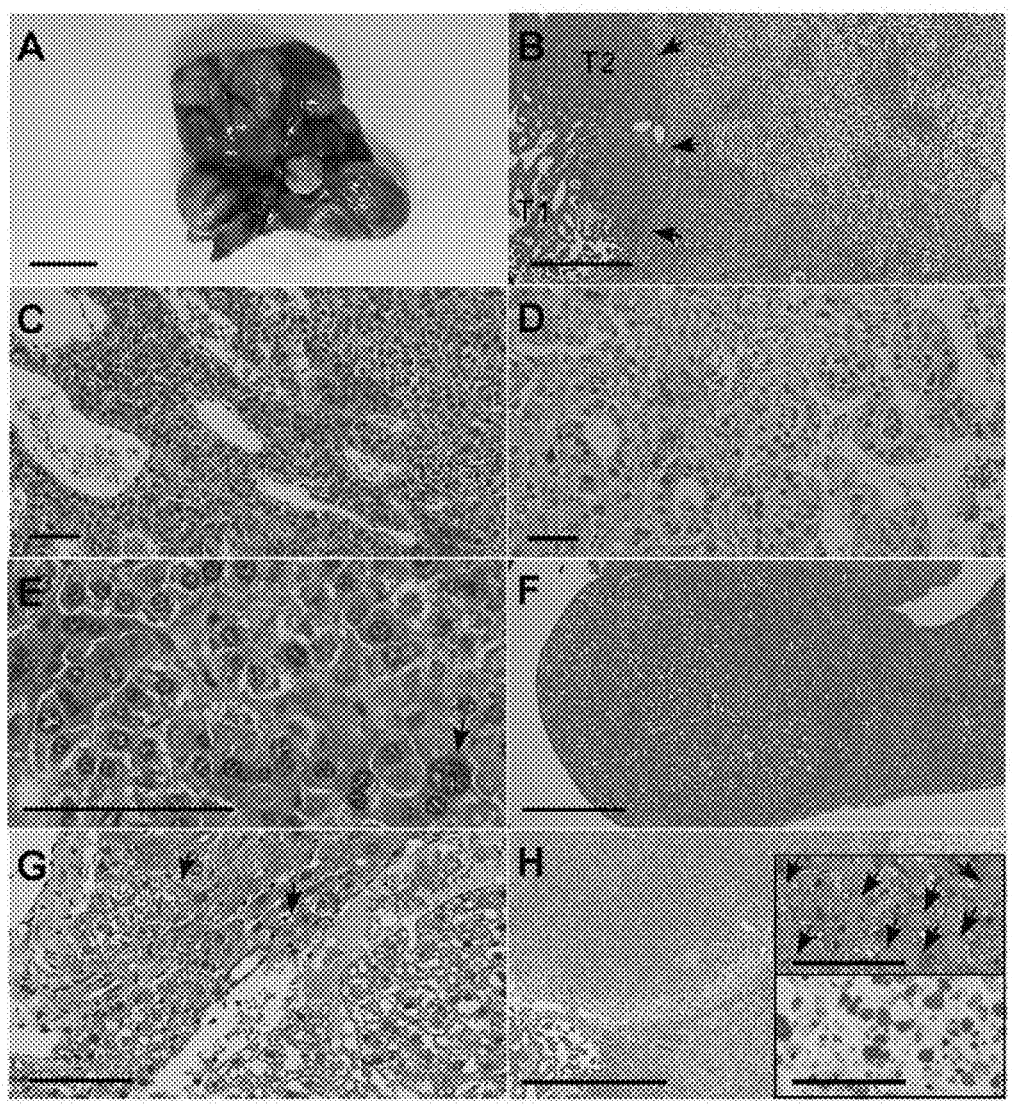
FIG. 9 shows mice transduced with AAV/HBV developed hepatocellular carcinoma (HCC). Wild-type C57BL/6 mice were transduced with AAV/HBV and sacrificed 12 to 16 months later (see Table 1 for details). The liver of each mouse was photographed, then prepared as paraffin sections for histological analysis.
Figure 12:
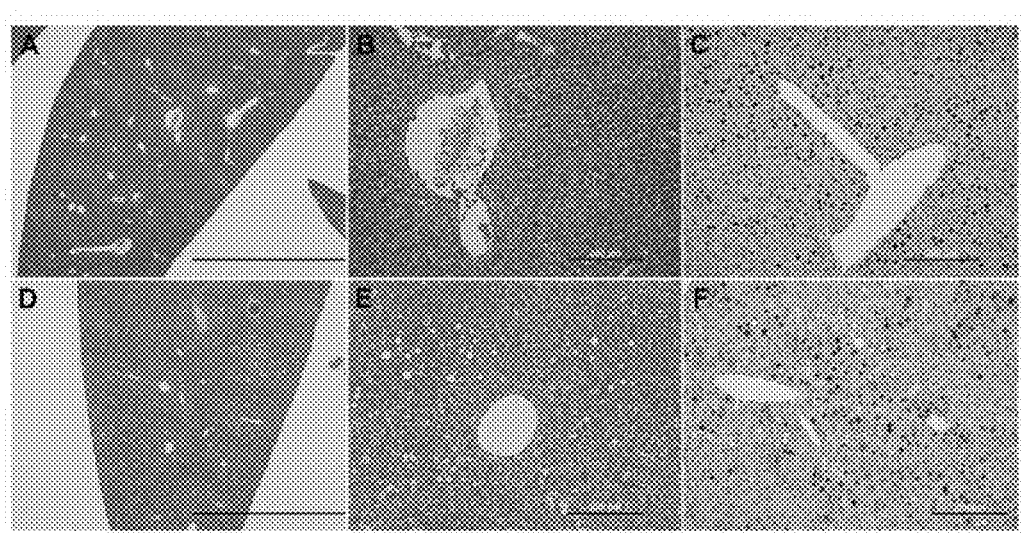
FIG. 12 shows no significant histological changes are seen in C57BL/6/HBV transgenic mice. AAV/GL2-transduced C57BL/6/HBV transgenic mice were sacrificed between 13 and 19.5 months after AAV transduction (see Table 1). Representative H&E-stained liver section show no apparent abnormalities in lobular architecture (FIGS. 12A, 12B, IF1226) or only mild irregular steatosis (FIGS. 12D, 12E, IF1421). Immunohistochemical staining revealed positive staining for HBc (FIGS. 12C, 12F).

Significantly, at between 12 and 16 months after AAV/HBV transduction, all mice developed liver tumor nodules (12 of 12), manifesting pathological features of either dysplasia (2 of 12) or HCC (10 of 12) (FIG. 9 and Table 1). The adjacent non-tumor liver tissue was also histologically abnormal, frequently displaying inflammatory infiltrates, steatosis, and focal necrosis (FIG. 10). Mild to moderate liver fibrosis was also occasionally observed. In contrast, none of the HBV transgenic mice (0 of 13) on the same C57BL/6 background treated with the same amount of a control AAV/GL2 vector developed tumor nodules in the liver (Table 1), which remained histologically normal or only displayed mild steatosis on microscopic analysis (FIG. 12). The fact that the HBV transgenic mice stably produced much higher levels of HBV virions and proteins (FIG. 8 and Table 1) than the AAV/HBV-transduced wild-type mice argues against a direct hepatocarcinogenic effect of the virus itself. AAV vectors have been found to integrate into host cell chromosomes in a non-specific manner, favoring transcriptionally active genes and DNA breakage sites. There have been reports that AAV-mediated gene therapy increases the risk of formation of liver tumors and that this is associated with AAV insertion and overexpression of the Rian gene, containing multiple small nucleolar RNAs, and of the Mirg gene, containing multiple microRNAs. However, our results (Table 1) and those from other studies, including a large-scale study of 695 mice, did not show any increased risk of developing liver tumors or other tumor types in AAV-treated mice. We also did not detect increased expression of the Rian and Mirg genes in AAV/HBV-induced tumors (unpublished results), arguing against a role of these two genes in hepatocarcinogenesis in our HCC model. Instead, our data support indirect carcinogenic effects of anti-HBV immune cells, present in the AAV/HBV-transduced mice, but not in the C57BL/6 HBV transgenic mice, through the induction of recurrent hepatic injury and regeneration, eventually leading to critical genetic alterations and HCC development. We are currently investigating which immune effector is responsible for HBV-associated hepatocarcinogenesis by AAV/HBV transduction of a panel of mouse lines with selective immunodeficiency.

Compared to HCC models established in genetically engineered mice involving either overexpression of oncogenic proteins or germline disruption of tumor suppressors, our AAV/HBV-transduced HCC model in mice has the advantage of easy manipulation and recapitulation of the immune effectors known to be critical in the development of human HBV-associated HCC. (Newell et al. (2008) "Experimental models of hepatocellular carcinoma" *J Hepatol* 48, 858-879; Keng et al. (2009) "A conditional transposon-based insertional mutagenesis screen for genes associated with mouse hepatocellular carcinoma" *Nat Biotechnol* 27, 264-274). We believe that our AAV/HBV-induced HCC model is more likely to reflect the heterogeneity of the molecular pathways that are dysregulated in human HCC. Because of the homogeneous genetic background of the inbred mice used in this study and the opportunity for sampling serial liver lesions in the preneoplastic and neoplastic stages, HCC developed in our AAV/HBV-transduced mice should greatly simplify the identification of cancer-causing mutations, providing an opportunity for developing novel therapeutic interventions. Moreover, we anticipate that a similar trans-splicing AAV technique could be applied to generate other viral disease mouse models, including chronic hepatitis C virus infection.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A non-human animal disease model for hepatitis B virus-associated liver disease, comprising a hepatitis B virus genome in the liver cells thereof and exhibiting at least one or more of the following symptoms:
   (a) expression of hepatitis B viral particles in the serum for more than 2 weeks;
   (b) hepatitis B viral DNA in the serum;
   (c) hepatitis B virus (HBV) envelope and HBV e proteins in the serum; and
   (d) expression of hepatitis B virus (HBV) core and HBV envelope proteins in the liver but not in the kidney, heart, lung, brain, pancreas, spleen, stomach or intestine tissues thereof,
   wherein the hepatitis B virus genome is transduced into the liver cells with an adenovirus-associated vector (AAV) comprising a hepatitis B virus genomic DNA insert.

2. The non-human animal disease model for hepatitis B virus (HBV)-associated liver disease of claim 1, further exhibiting at least one of the following serological and immunological responses m the serum:
   (a) HBV envelope antigen;
   (b) hepatitis B e antigen: and
   (c) an increase in hepatitis B envelope-specific CD8+T cells in the liver and/or spleen as compared to a control animal without the hepatitis B virus genome in the liver cells thereof.

3. The non-human animal disease model for hepatitis B virus (HBV)-associated liver disease of claim 2, further exhibiting a chronic hepatitis B serological profile as follows:
   (a) negative for anti-hepatitis B envelope antibody;
   (b) negative for anti-hepatitis B e antibody; and
   (c) positive for anti-hepatitis B core antibody.

4. The non-human animal disease model for hepatitis B virus (HBV)-associated liver disease of claim 2, further exhibiting at least one of the following immunopathological responses:
   (a) inflammatory infiltration in the liver tissues:
   (b) mitosis in the liver tissues;
   (c) acidophilic nuclear inclusions in the hepatocytes;
   (d) expression of hepatitis B core protein in the hepatocytes;
   (e) expression of hepatitis B envelope protein in the hepatocytes; and
   (f) an increase in the level of alanine aminotransferase as compared to that of a control animal without the hepatitis B virus genome in the liver cells thereof.

5. The non-human animal disease model for hepatitis B virus (HBV)-associated liver disease of claim 1, wherein the animal disease model is a mouse chosen from BALB/c, ICR, C57BL/6 and FVB strains.

6. The non-human animal disease model for hepatitis B virus (HBV)-associated liver disease of claim 1, wherein the animal disease model is a rodent.

7. The non-human animal disease model for hepatitis B virus (HBV)-associated liver disease of claim 6, wherein the animal disease model is immune competent.

8. The non-human animal disease model for hepatitis B virus-associated liver disease of claim 4, further exhibiting one or more liver pathological symptom chosen from:
   (a) necrosis of hepatocytes; and
   (b) liver tumor nodules.

9. The non-human animal disease model of claim 8, wherein the hepatitis B virus-associated liver disease is hepatocellular carcinoma and the animal disease model exhibits at least one of following liver pathological changes:
   (a) positive for fibrinogen in the liver tissues;
   (b) liver dysplasia; and
   (c) liver fibrosis.

10. A non-human animal disease model for hepatocellular carcinoma, comprising a hepatitis B virus genome in the liver cells thereof and exhibiting at least one of the following symptoms:
    (a) liver tumor nodules;
    (h) liver dysplasia;
    (c) inflammatory infiltrates in the liver;
    (d) steatosis and necrosis of hepatocytes;
    (e) liver fibrosis; and
    (f) an increase in the level of alanine aminotransferase as compared to that of a control animal without the hepatitis B virus genome,
    wherein the hepatitis B virus Genome is transduced into the liver cells with an adenovirus-associated vector (AAV) comprising a hepatitis B virus genomic DNA insert.

11. The non-human animal disease model for hepatitis B virus-associated liver disease of claim 1, whose germ line does not comprise a hepatitis B virus genome.

12. A non-human animal disease model for hepatitis B virus-associated liver disease, comprising a hepatitis B virus genome in the liver cells thereof and exhibiting at least one or more of the following symptoms;
    (a) expression of hepatitis B viral panicles in the serum for more than 2 weeks;
    (b) hepatitis B viral DNA in the serum;
    (c) hepatitis B virus (HBV) envelope and HBV e proteins in the serum; and
    (d) expression of hepatitis B virus (HBV) core and HBV envelope proteins in the liver but not in the kidney, heart, lung, brain, pancreas, spleen, stomach or intestine tissues thereof, wherein the hepatitis B virus genome is transduced into the liver cells with two adeno-associated virus (AAV) vectors, each carrying a different fragment of the HBV genome, which together produce a functional HBV genome in the liver cells thereof.

13. A method for screening for a therapeutic agent effective in treating hepatitis B virus-associated liver disease, comprising:
(a) providing a non-human animal disease model for hepatitis B virus-associated liver disease according to claim 1;
(b) administering to the animal disease model an agent to be tested for therapeutic effectiveness; and
(c) determining whether the agent is effective for treating the hepatitis B virus-associated liver disease.

14. A method for screening for a therapeutic agent effective in treating hepatocellular carcinoma, comprising:
(a) providing a non-human animal disease model for hepatitis B virus-associated liver disease according to claim 8;
(b) administering to the animal disease model a compound to be tested for therapeutic effectiveness; and
(c) determining whether the compound is effective for treating the hepatocellular carcinoma.

15. A method of screening for a therapeutic agent effective in treating hepatocellular carcinoma, comprising:
(a) providing a non-human animal disease model for hepatitis B virus-associated liver disease according to claim 9;
(b) administering to the animal disease model a compound to be tested for therapeutic effectiveness; and
(c) determining whether the compound is effective for treating the hepatocellular carcinoma.

16. A method of screening for a therapeutic agent effective in treating hepatocellular carcinoma, comprising:
(a) providing a non-human animal disease model for hepatitis B virus-associated liver disease according to claim 10;
(b) administering to the animal disease model a compound to be tested for therapeutic effectiveness; and
(c) determining whether the compound is effective for treating the hepatocellular carcinoma.

17. A method of generating a non-human animal disease model for hepatitis B virus-associated liver disease according to claim 12, comprising:
(a) obtaining a non-human animal; and
(b) administering to the animal a composition comprising: a first adeno-associated viral vector comprising 5' genomic DNA fragment of a hepatitis B virus, and a second adeno-associated viral vector comprising 3' genomic DNA fragment of the hepatitis B virus; and
(c) allowing the animal develops symptoms associated with the hepatitis B virus-associated liver disease.

18. The method of claim 17, wherein the administering step is replaced by:
administering to the animal a composition comprising an adeno-associated viral vector comprising a hepatitis B virus genomic DNA.

19. The method of claim 17, wherein the non-human animal is an immune competent mouse.

* * * * *